(12) United States Patent
Early et al.

(10) Patent No.: US 9,125,695 B2
(45) Date of Patent: Sep. 8, 2015

(54) ANKLE FUSION NAIL APPARATUS AND METHOD

(71) Applicants: John S. Early, Dallas, TX (US); Greg Pomeroy, Cape Elizabeth, ME (US)

(72) Inventors: John S. Early, Dallas, TX (US); Greg Pomeroy, Cape Elizabeth, ME (US)

(73) Assignee: BESPA, Inc., Dallas, TX (US)

( * ) Notice: Subject to any disclaimer, the term of this patent is extended or adjusted under 35 U.S.C. 154(b) by 0 days.

(21) Appl. No.: 13/573,985

(22) Filed: Oct. 18, 2012

(65) Prior Publication Data

US 2014/0114313 A1  Apr. 24, 2014

(51) Int. Cl.
*A61B 17/58* (2006.01)
*A61B 17/72* (2006.01)

(52) U.S. Cl.
CPC ......... *A61B 17/7225* (2013.01); *A61B 17/7291* (2013.01)

(58) Field of Classification Search
CPC ............... A61B 17/72; A61B 17/1725; A61B 17/7225; A61B 17/7223; A61B 17/7291; A61B 17/7208; A61B 17/7241
USPC .................. 606/62, 63, 64, 65, 284
See application file for complete search history.

(56) References Cited

U.S. PATENT DOCUMENTS

| | | | | |
|---|---|---|---|---|
| 2002/0183750 A1* | 12/2002 | Buhler | ............................ | 606/62 |
| 2003/0097131 A1* | 5/2003 | Schon et al. | .................... | 606/62 |
| 2006/0235394 A1* | 10/2006 | Martin | ............................ | 606/62 |
| 2009/0062796 A1* | 3/2009 | Parks et al. | ..................... | 606/62 |
| 2009/0306664 A1* | 12/2009 | Teeny | ............................ | 606/64 |
| 2010/0010490 A1* | 1/2010 | Brigido | .......................... | 606/64 |
| 2011/0004212 A1* | 1/2011 | Gall et al. | ..................... | 606/62 |
| 2011/0054473 A1* | 3/2011 | Brigido | ......................... | 606/62 |
| 2011/0251614 A1* | 10/2011 | Piraino | ......................... | 606/62 |
| 2012/0065638 A1* | 3/2012 | Moore | ............................ | 606/62 |

* cited by examiner

*Primary Examiner* — Jerry Cumberledge
*Assistant Examiner* — Tessa Matthews
(74) *Attorney, Agent, or Firm* — J. Nevin Shaffer, Jr.

(57) ABSTRACT

An ankle fusion nail apparatus and method includes a first, tibial component that includes a hole there through. The tibial component includes, among other things, a base. A second, talar component includes a hole there through, also, and, among other things, a base and a top. The tibial component is separate from the talar component. A third, central component is provided that is separate from the first tibial component and the second talar component. The central component is conformed to connect with the tibial base and the talar top such that the central component joins the tibial and talar components together and aligns them as the central component is connected with the tibial base and the talar top.

13 Claims, 3 Drawing Sheets

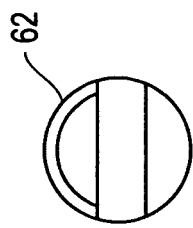
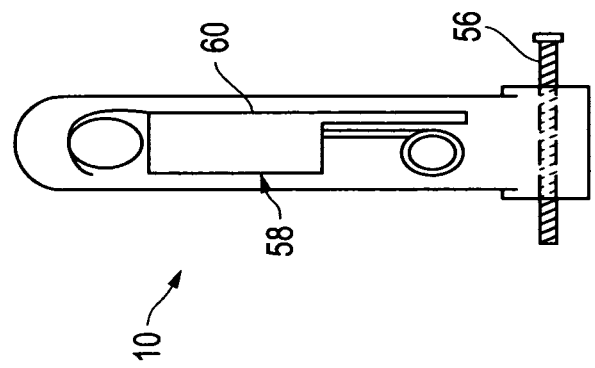
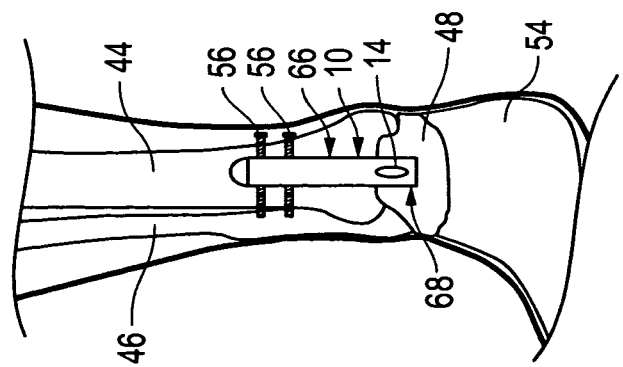

ANKLE FUSION NAIL APPARATUS AND METHOD

FIELD OF THE INVENTION

This invention relates to an ankle fusion apparatus and method. In particular, in accordance with one embodiment, the invention relates, to an ankle fusion nail apparatus including a first, tibial component that includes a hole there through. The tibial component includes, among other things, a base. A second, talar component includes a hole there through, also, and, among other things, a base and a top. The tibial component is separate from the talar component. A third, central component is provided that is separate from the first tibial component and the second talar component. The central component is conformed to connect with the tibial base and the talar top such that the central component joins the tibial and talar components together and aligns them as the central component is connected with the tibial base and the talar top.

BACKGROUND OF THE INVENTION

Ankle fusion is a routinely performed operation to relieve pain in the ankle due to bone or joint destruction from injury or disease. The prior art includes a variety of approaches used as well as a variety of fixation methods. All fixation methods require a standard debridement of the area to be fused; removal of cartilage, dead bone, and fibrous tissue to get good contact between healthy bone surfaces.

Presently, when the two bone halves are ready to be fixed together, the surgeon chooses a method to hold the two bones together until the bone can grow together. The prior art methods used include external fixation where pins stick out from the bones and are joined by external compression rods or frames. Simple screw fixation, much like in carpentry, can be used with the screw going from one bone to the other to lock the two pieces together. There are also a number of prior art metal plates (titanium or stainless steel) which can be applied to the exposed bone surface of the tibia and talus. The plates cross between the two bones and screws are used to fix the metal plate to each bone.

There are also so called "intramedullary nails" which are touted as "ankle fusion nails" but, in fact, do not meet the criteria for such a device as will be disclosed herein. To date, however, the prior art intramedullary nail is solid bar or hollow pipe that is placed in the center of the tibia or leg bone and travels in the medullary canal or inside the leg bone. The prior art nails, however, actually fuse both of the joints in the hindfoot as practiced. This is very detrimental to the long term survival of the foot. An advantage of the nail, however, is that it is wholly inside the leg bone and thus creates greater stability than an outside plate and creates a smaller lever arm for deforming forces. A very big disadvantage of the prior art nails, however, is that they destroy adjacent joints and they are not easily adjustable to provide appropriate and necessary compression of the two bones surfaces.

Thus, it is an object of this invention to provide an ankle fusion nail system and method that is an intramedullary device that provides stabilization and fixation during boney healing without violating surrounding joints, that does not fuse the whole hindfoot and that allows for a limited incision thus minimizing soft tissue damage. It is a further object of the invention to provide an ankle fusion nail that is adjustable such that the necessary compression of the two bone surfaces may be accurately and precisely applied by the nail itself.

SUMMARY OF THE INVENTION

Accordingly, the ankle fusion nail apparatus and method of the present invention, according to one embodiment includes a first, tibial component including a hole there through, the tibial component including a base. A second, talar component includes a hole there through, the talar component including a base and a top and is separate from the talar component. A third, central component separate from the first tibial component and the second talar component is provided, in which the central component is conformed to connect with the tibial base and the talar top such that the central component joins the tibial and talar components together as the central component is connected with the tibial base and the talar top.

All terms used herein are given their common meaning as known generally and to those in the art.

According to one aspect of the invention, the tibial component includes two holes there through approximately perpendicular to the tibial component and spaced angularly apart from each other. In another aspect, the talar component is hollow and the central component and the tibial component are at least partially hollow such that a passageway is created between the talar component and the central component and the tibial component when the central component is connected with the talar component and the tibial component. In one aspect, a compression device is provided and the passageway provides access to the compression device for drawing the tibial component and the talar component together.

In another aspect of the invention, a fourth, elbow component is provided where the elbow component includes a first end and a second end and where the first end and the second end are connected at approximately ninety degrees and where the first end is conformed to connect with the base of the talor component. In another aspect, the elbow component includes at least one screw hole and the second end of the elbow component is conformed to connect with a separate tibial component.

In another aspect, the base of the first, tibial component includes a female receptor conformed to connect with a male connector on the third, central component. In a further aspect, the second, talar component includes a male connector conformed to connect with a female receptor on the third, central component.

In one aspect, an adjustable sleeve is provided that fits within the connected first, second and third components. In another aspect the adjustable sleeve is adjustable to provide axial compression to said connected first, second and third components.

In a further aspect, the two holes in the tibial component are spaced angularly apart from each other by approximately forty-five degrees.

According to another embodiment of the invention, an ankle fusion nail apparatus includes a first, tibial component including a hole there through, the tibial component including a base. A second, talar component including a hole there through, the talar component including a base and a top and separate from the tibial component. A third, central component separate from the first, tibial component and the second, talar component, where the central component is conformed to connect with the tibial base and the talar top such that the central component pulls the components together as the central component is connected with the tibial base and the talar top and such that the three separate components once connected align along a common axis. And an adjustable sleeve is provided that is connected with the connected three components such that adjustment of the adjustable sleeve provides axial compression to the ankle fusion nail.

In one aspect, the tibial component includes two holes there through approximately perpendicular to the tibial component and spaced angularly apart from each other. In another aspect, the two holes are spaced angularly apart from each other by approximately forty-five degrees.

In another aspect of the invention, a fourth, elbow component is provided where the elbow component includes a first end and a second end and where the first end and the second end are connected at approximately ninety degrees and where the first end is conformed to connect with the base of the talor component. In another aspect, the elbow component includes at least one screw hole and the second end of the elbow component is conformed to connect with a separate tibial component.

In another aspect, the base of the first, tibial component includes a female receptor conformed to connect with a male connector on the third, central component and, in another aspect, the second, talar component includes a male connector conformed to connect with a female receptor on the third, central component.

According to another embodiment of the invention, a method for fusing an ankle using an ankle fusing nail includes the steps of:

a. providing a first, tibial component including a hole there through, the tibial component including a base; a second, talar component including a hole there through, the talar component including a base and a top and is separate from said tibial component; and a third, central component separate from the first tibial component and the second talar component, where the central component is conformed to connect with the tibial base and the talar top such that the central component joins and aligns the components together as the central component is connected with the tibial base and the talar top;

b. inserting the tibial component in a tibia and connecting the tibial component with the tibia;

c. inserting the talar component in a talar and connecting the talar component with the talar; and d. connecting the central component with the talar component and with the tibial component.

In another aspect of this invention, the method further includes the step of providing a compression device connected with the three connected components and adjusting the compression device so as to assert axial compression to the three connected components.

In another aspect, prior to insertion of the tibial component, the method includes the step of creating a tibial cavity intramedullary in the tibia such that the tibial cavity aligns with a talar cavity created in the talar, the tibial cavity created such that the tibial cavity passes in front of a subtalar joint.

In a further aspect, prior to insertion of the talar component the talar cavity is created where the talar cavity in the talar extends into the talar neck.

In one aspect, the tibial component includes two holes there through approximately perpendicular to the tibial component and spaced angularly apart from each other. In one aspect, the invention further includes providing a fourth, elbow component where the elbow component includes a first end and a second end and where the first end and the second end are connected at approximately ninety degrees and where the first end is conformed to connect with the base of the talor component and inserting the elbow component in the talar. In another aspect, the elbow component includes at least one screw hole and where the second end of the elbow component is conformed to connect with a separate tibial component and includes the step of inserting the separate tibial component in the talar, connecting the elbow component with the separate tibial component on the second end of the elbow component and securing the elbow component in place with a screw through the at least one screw hole.

In one aspect, the base of the first, tibial component includes a female receptor conformed to connect with a male connector on the third, central component and the second, talar component includes a male connector conformed to connect with a female receptor on the third, central component.

DESCRIPTION OF THE DRAWINGS

Other objects, features and advantages of the present invention will become more fully apparent from the following detailed description of the preferred embodiment, the appended claims and the accompanying drawings in which:

FIG. 3 is a front view of the invention of FIG. 2 showing the two screws in the tibia;

FIG. 4 is a side view of the ankle fusion nail including the compression device;

FIG. 5 is an end view of the ankle fusion nail of FIG. 4 showing the compression adjustment gear;

DETAILED DESCRIPTION OF THE INVENTION

Figure 2:
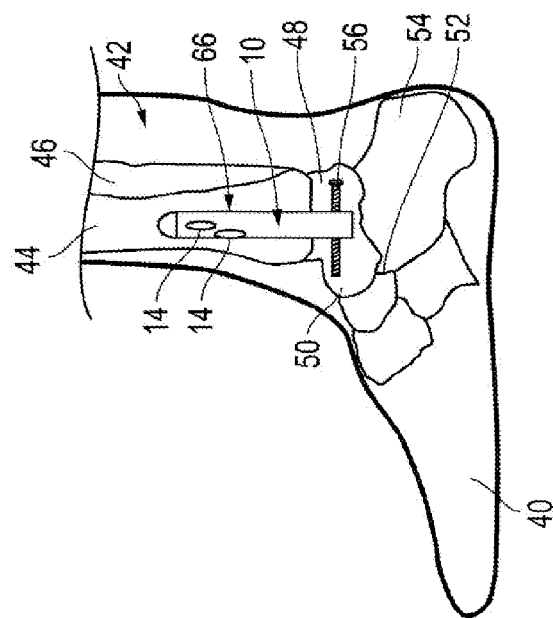
FIG. 2 is a is a side view showing the invention of FIG. 1 in place in the ankle and leg and showing the single screw in the talar.
Figure 1:
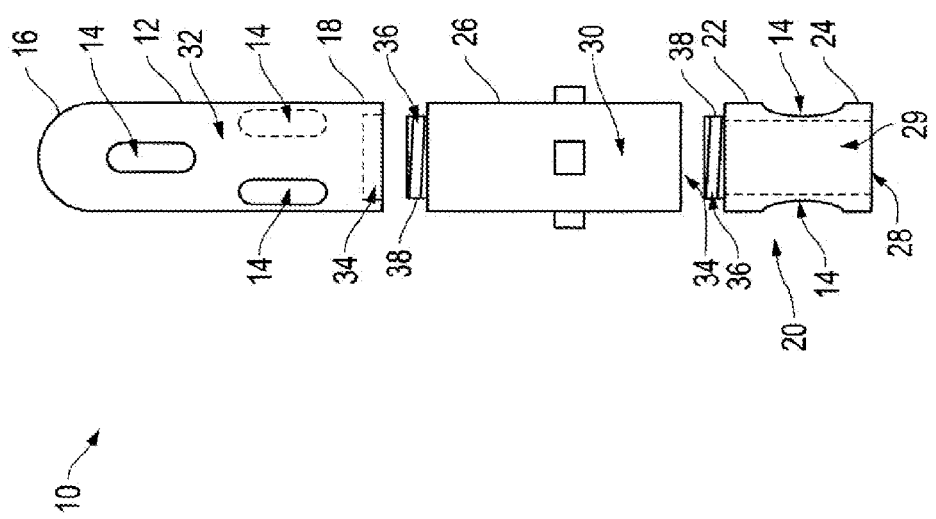
FIG. 1 is an exploded view of the ankle fusion nail of the present invention in which the three separate components of the nail are illustrated.

The preferred embodiment of the present invention is illustrated by way of example in FIGS. 1-8. With specific reference to FIG. 1, ankle fusion nail 10 includes a first, tibial component 12. Tibial component 12 includes a hole 14 that passes through the tibial component 12. In general, hole 14 passes approximately perpendicular to the axis of tibial component 12. That is, as illustrated, tibial component 12 has a length from the top 16 to the base 18 that forms the longitudinal axis. Hole 14 passes across that longitudinal axis as illustrated. According to one embodiment, more than one hole 14 is provided in tibial component 12 as shown. Preferably, the two holes 14 are spaced apart angularly and on separate plains from each other. The Applicants have found that a spacing of forty-five degrees provides the best stabilization.

A second, talar component 20 includes a top 22 and base 24. Talar component 20 is a separate, individual component apart from tibial component 12. Talar component 20 also includes a hole 14 that passes through talar component 20 as illustrated.

A third, central component 26 is provided that is also a separate, individual component. Central component 26, however, is conformed to connect with tibial component 12 and talar component 20. Once connected, central component 26 secures the three separate components together and aligns them one with each other.

According to one aspect, once connected, a passageway 29 is formed by the combination of the hollow inside 28 of talar component 20 in combination with the at least partially hollow inside 30 and 32 of central component 26 and tibial component 12. Passageway 29 provides access to the inside of ankle fusion nail from the open base 24 of talar component 20, as will be described more fully hereafter.

According to a preferred embodiment, base 18 of tibial component 12 includes a female receptor 34 (shown in dotted lines). Female receptor 34 preferably consists of grooves (not shown) conformed to connect with male connector 36 in the form of threads 38 of central component 26. As is known, threads 38 are inserted into female receptor 34 and rotated to make the connection. Any, female/male connector system now know or hereafter developed is included within the proper scope of the invention.

Likewise, according to a preferred embodiment, top 22 of talar component 20 includes a male connector 36 with threads 38 that are conformed to connect with female receptor 34 in central component 26. Again, the three separate components of the ankle fusion nail 10 of the present invention are connected and aligned by means of central component 26.

Referring now to FIGS. 2 and 3, the ankle fusion nail 10 is shown in place within a human foot 40 and leg 42. Leg 42 includes tibia 44 and fibula 46. The pertinent parts of foot 40 are talus bone 48. Talus bone 48 includes teslas neck 50 and subtalar joint 52. FIG. 2 also shows heel bone or calcaneus 54.

FIG. 2 shows screw 56 passing through talar component 20 by means of hole 14 within talus 48 and into talus neck 50. FIG. 3 shows two screws 56 passing through spaced apart and angularly spaced holes 14 in tibial component 12 within tibia 44. Again, Applicants have determined that requiring this oblique spacing of holes 14 allows the ankle fusion nail 10 to be dynamic in its axial stabilization but rigid in its rotational fixation. Preferably, these two screws 56 are set forty-five degrees apart to stabilize the ankle fusion nail 10 in the distal tibia 44 as illustrated.

Referring now to FIGS. 4 and 5 another element of the invention is illustrated. In this instance a compression device 58 is provided. As noted herein, a significant failing of prior art devices and an important attribute of the present invention is a system to provide axial compression to the tibia 44 and talus bone 48 to ensure proper bone growth and healing. In some respects this axial compression is provided when central component 26 is joined with tibial component 12 and talar component 20. Additional adjustable compression is provided by means of adjustable sleeve 60. Adjustable sleeve 60 is located within the hollow inside passageway 29 formed by the combination of the three separate components as described above. Adjustable sleeve 60 is operated by action of gear 62. Gear 62 is accessed through the base 24 of talar component 20. A screwdriver (not shown) is inserted to turn gear 62 which draws adjustable sleeve 60 down forcing ankle fusion nail 10 into the tibia 44 and pulling up on talar component 20 which compresses the fusion site where the two bones come together.

By way of further description, the ankle fusion nail 10 presented herein is truly and intramedullary nail for fusion of the ankle only. It fuses the ankle only by ensuring it is used in cavities 64 that are properly positioned. Referring again to FIGS. 2 and 3, a drill guide (not shown) is used to align the tibia 44 and talus bone 48 so that the tibial cavity 66 is located intramedullary within tibia 44 and in front of the subtalar joint 52 as illustrated. Once the tibial cavity 66 is created from the bottom of the foot 40 in front of the subtalar joint 52 and into the center of the leg bone, tibia, 44, the talar cavity 68 is created as best seen in FIG. 3.

Figure 6:
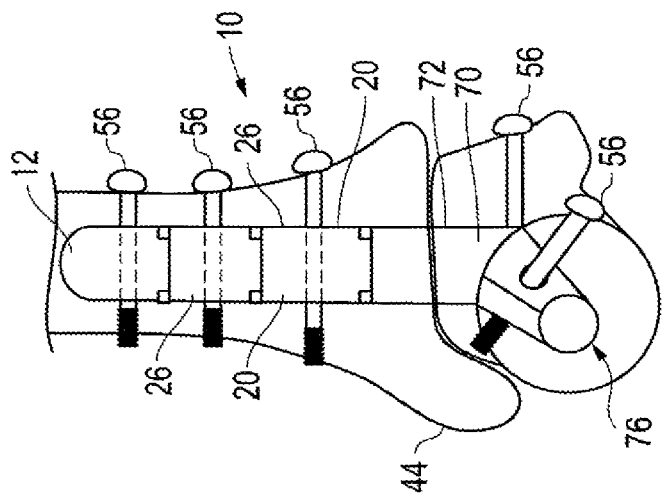
FIG. 6 is a side view of the fourth, elbow component in combination with the invention of FIG. 1.
Figure 7:
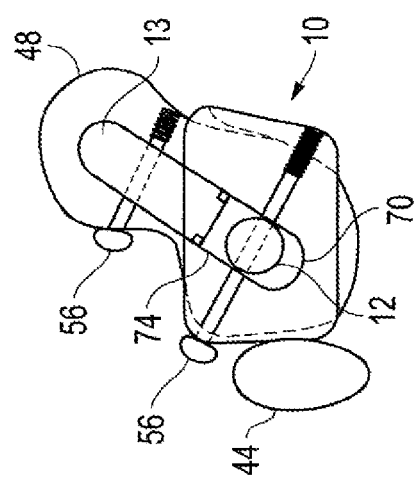
FIG. 7 is a top view of the invention of FIG. 6.
Figure 8:
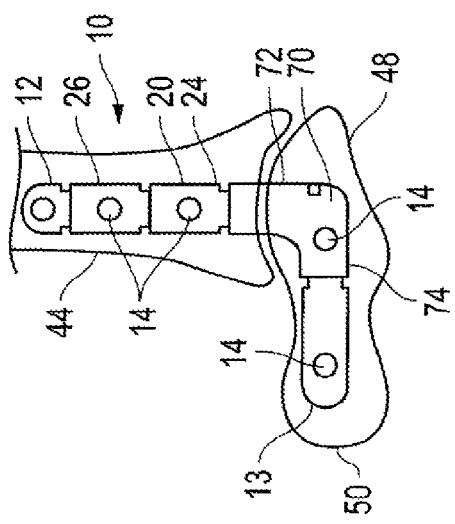
FIG. 8 is an rear view of the invention of FIG. 6 with screws in place.

According to another embodiment of the invention, a fourth component is provided. Referring now to FIGS. 6-8, the fourth, elbow component 70 is, preferably, tubular in shape as are the other components. Elbow component 70 is, as its name suggests and FIG. 6 reveals, a bent form, bent approximately ninety degrees from first end 72 to second end 74. Ends 72 and 74 include threads (not shown) for connection with other components. In a preferred embodiment, end 72 is connected with talor component 20 at base 24. End 74 of elbow component 70 is conformed to connect with a second tibial component 13. In this case tibial component 13 is located in the talus neck 50, however, and not the tibia 44. The structure and function of first and second tibial components 12 and 13 are the same, it is just their location that is different as shown in the figures. Elbow component 70 includes at least one hole 14 through which a locking screw 56 may pass. Elbow component 70 may include guides for alignment and access ports for wrenches and screw drivers to assist with connection with other components. These features may be of any type as described herein or as known hereafter and are well within the ordinary skill level of those in the art and are not described more fully hereafter.

When present, the preparation for use of the elbow component 70 requires that a talor shaft 76 be prepared using a drill guide designed to fit into the vertical hole created in the dome of the talus 48 for the tibial shaft as described above. The drill is used to create a talor shaft 76 from the posterior lateral corner of the talus bone 48 down towards the talus neck 50. The length of the talor shaft 76 is conformed to match the length of the components to be inserted therein.

Once the talor shaft 76 is completed, assembly of the ankle fusion nail 10 proceeds with assembly of the tibial components first. The second tibial component 13 is then connected with the second end 74 of elbow component 70. Then the first end 72 of the elbow component 70 is connected with base 24 of talor component 20. At that point, one screw 56 is screwed into talus bone 48 through hole 14 in elbow component 70. Also, preferably, one screw 56 is screwed into talus bone 48 through hole 14 in tibial component 13 for securing and stabilizing the ankle fusion nail 10. Thereafter, bone grafts may be placed in holes, as appropriate and available, and the surgical wound closed and dressings applied.

The description of the present embodiments of the invention has been presented for purposes of illustration, but is not intended to be exhaustive or to limit the invention to the form disclosed. Many modifications and variations will be apparent to those of ordinary skill in the art. As such, while the present invention has been disclosed in connection with an embodiment thereof, it should be understood that other embodiments may fall within the spirit and scope of the invention as defined by the following claims.

What is claimed is:

1. An ankle fusion nail apparatus comprising:
   a. a first, tibial component including a hole there through, said tibial component including a base;
   b. a second, talar component including a hole there through, said talar component including a base and a top and is separate from said tibial component;
   c. a third, central component separate from said first tibial component and said second talar component, wherein said central component is conformed to connect with said tibial base and said talar top such that said central component joins said tibial and talar components together as said central component is connected with said tibial base and said talar top; and
   d. a fourth, elbow component wherein said elbow component includes a first end and a second end and wherein said first end and said second end are connected at approximately ninety degrees such that a permanent non-flexible elbow is formed and wherein said first end is conformed to connect at said base of said talar component such that the first end is aligned below said base and said second end extends outwardly from below said base at the approximately ninety degree connection and wherein said talar component is hollow and said central component and said tibial component and said elbow component are at least partially hollow such that a rigid, non-flexible structure is created with a passageway between said talar component and said central component and said tibial component and said elbow component when said central component is connected with said talar component and said tibial component and said elbow component is connected with said talar component.

2. The apparatus of claim 1 wherein said tibial component includes two holes there through approximately perpendicular to said tibial component and spaced angularly apart from each other.

3. The apparatus of claim 2 wherein said two holes are spaced angularly apart from each other by approximately forty-five degrees.

4. The apparatus of claim 1 further including a compression device wherein said passageway provides access to said compression device for drawing the tibial component and the talar component together.

5. The apparatus of claim 1 wherein said elbow component includes at least one screw hole and wherein said second end of said elbow component is conformed to connect with a separate tibial component.

6. The apparatus of claim 1 further including an adjustable sleeve that fits within the connected first, second and third components.

7. The apparatus of claim 6 wherein said adjustable sleeve is adjustable to provide axial compression to said connected first, second and third components.

8. The apparatus of claim 1 wherein said first element, said second element, said third element and said fourth element are tubular in shape and of the approximately same diameter.

9. An ankle fusion nail apparatus comprising:
  a. a first, tibial component including a hole there through, said tibial component including a base;
  b. a second, talar component including a hole there through, said talar component including a base and a top and is separate from said tibial component;
  c. a third, central component separate from said first, tibial component and said second, talar component, wherein said central component is conformed to connect with said tibial base and said talar top such that said central component pulls said components together as said central component is connected with said tibial base and said talar top and such that the three separate components once connected align along a common axis;
  d. an adjustable sleeve connected with said connected three components such that adjustment of said adjustable sleeve provides axial compression to said ankle fusion nail; and
  d. a fourth, elbow component wherein said elbow component includes a first end and a second end and wherein said first end and said second end are connected at approximately ninety degrees such that a permanent non-flexible elbow is formed and wherein said first end is conformed to connect at said base of said talar component such that the first end is aligned below said base and said second end extends outwardly from below said base at the approximately ninety degree connection and wherein said talar component is hollow and said central component and said tibial component and said elbow component are at least partially hollow such that a rigid, non-flexible structure is created with a passageway between said talar component and said central component and said tibial component and said elbow component when said central component is connected with said talar component and said tibial component and said elbow component is connected with said talar component.

10. The apparatus of claim 9 wherein said tibial component includes two holes there through approximately perpendicular to said tibial component and spaced angularly apart from each other.

11. The apparatus of claim 9 wherein said elbow component includes at least one screw hole and wherein said second end of said elbow component is conformed to connect with a separate tibial component.

12. The apparatus of claim 9 wherein said second, talar component includes a hole there through approximately perpendicular to said talar component.

13. The apparatus of claim 9 wherein said first element, said second element, said third element and said fourth element are tubular in shape and of the approximately same diameter.

* * * * *

UNITED STATES PATENT AND TRADEMARK OFFICE
CERTIFICATE OF CORRECTION

| | | |
|---|---|---|
| PATENT NO. | : 9,125,695 B2 | Page 1 of 1 |
| APPLICATION NO. | : 13/573985 | |
| DATED | : September 8, 2015 | |
| INVENTOR(S) | : John S. Early et al. | |

It is certified that error appears in the above-identified patent and that said Letters Patent is hereby corrected as shown below:

IN THE SPECIFICATION

In column 5, Line 19 "teslas neck" should read -- talus neck --.

Signed and Sealed this
Twenty-second Day of March, 2016

Michelle K. Lee
*Director of the United States Patent and Trademark Office*